(12) United States Patent
Naroditsky et al.

(10) Patent No.: US 8,355,790 B2
(45) Date of Patent: Jan. 15, 2013

(54) TRANSCUTANEOUS ELECTRICAL THERAPEUTIC DEVICE

(75) Inventors: Michael Naroditsky, Karmiel (IL); Hector Rotstein, Haifa (IL)

(73) Assignee: Nervomatrix Ltd, Netanya (IL)

( * ) Notice: Subject to any disclaimer, the term of this patent is extended or adjusted under 35 U.S.C. 154(b) by 518 days.

(21) Appl. No.: 12/301,464

(22) PCT Filed: May 31, 2007

(86) PCT No.: PCT/IL2007/000661
§ 371 (c)(1),
(2), (4) Date: Nov. 19, 2008

(87) PCT Pub. No.: WO2007/138595
PCT Pub. Date: Dec. 6, 2007

(65) Prior Publication Data
US 2009/0198305 A1    Aug. 6, 2009

Related U.S. Application Data

(60) Provisional application No. 60/809,299, filed on May 31, 2006.

(51) Int. Cl.
*A61N 1/00* (2006.01)
*A61B 5/04* (2006.01)
(52) U.S. Cl. ............... 607/46; 607/48; 600/372
(58) Field of Classification Search .............. 607/46, 607/48; 600/372
See application file for complete search history.

(56) References Cited

U.S. PATENT DOCUMENTS

| | | | |
|---|---|---|---|
| 4,838,272 A | 6/1989 | Lieber | |
| 5,070,873 A | 12/1991 | Graupe et al. | |
| 5,560,372 A | 10/1996 | Cory | |
| 6,141,575 A * | 10/2000 | Price | 600/372 |
| 6,564,079 B1 | 5/2003 | Cory et al. | |
| 6,850,795 B2 * | 2/2005 | Hoium et al. | 600/516 |
| 2002/0188332 A1 | 12/2002 | Lurie et al. | |
| 2003/0135245 A1 | 7/2003 | Campos | |
| 2004/0147977 A1 * | 7/2004 | Petrofsky | 607/50 |
| 2006/0047194 A1 * | 3/2006 | Grigorov | 600/372 |

OTHER PUBLICATIONS

International Search Report for parallel PCT application PCT/IL2007/000661, issued by USPTO with mailing date of Jun. 11, 2008 and published as WO 2007/138595 A3 on Apr. 23, 2009.
M. W. Flowerdew and J. G. Gadsby, "A review of the treatment of chronic low back pain with acupuncture-like transcutaneous electrical nerve stimulation and transcutaneous electrical nerve stimulation", Complementary Therapies in Medicine, vol. 5, published 1997, pp. 193-201.
G. Gernignani, I. Olivieri, G. Ruju and G. Pasero, "Transcutaneous electrical nerve stimulation in ankylosing spondylitis: a double-blind study", Arthritis and Rheumatology, vol. 34, published 1991, pp. 788-789.
M.I. Johnson, "The analgesic effects and clinical use of acupuncture-like TENS (AL-TENS)", Physical Therapy Reviews, vol. 3, published 1998, pp. 73-93.

(Continued)

*Primary Examiner* — Nicole F Lavert
(74) *Attorney, Agent, or Firm* — Simon Kahn

(57) ABSTRACT

An apparatus and method for locating therapeutically active points and applying transcutaneous electrical stimulation thereto are disclosed.

The apparatus includes patient applied therapeutic module, consisting of a fixture and a plurality of probes, and an actuating controlling module. The method including the steps of measuring local electrical impedances of a given skin surface area, identifying the points characterized by lower impedances, selecting the desired point/s and applying transcutaneous electrical stimulation thereto.

15 Claims, 11 Drawing Sheets

OTHER PUBLICATIONS

M.I. Johnson, "Transcutaneous electrical nerve stimulation (TENS) in the management of labour pain: the experience of over ten thousand women", British Journal of Midwifery, vol. 5, published 1997, pp. 400-405.

M.I. Johnson, C.H. Ashton, and J.W. Thompson, "An in-depth study of long term users of Transcutaneous electrical nerve stimulation (TENS). Implications for clinical use of TENS" Pain, vol. 44, published 1991 by Elsevier Science Publishers, pp. 221-229.

M.I. Johnson, C.H. Ashton, and J.W. Thompson, "Long term use of transcutaneous electrical nerve stimulation at Newcastle Pain Relief Clinic", Journal of the Royal Society of Medicine, vol. 85, published May 1992, pp. 267-268.

R. Melzack, P. Vetere, L. Finch, "Transcutaneous electrical nerve stimulation for low back pain. A comparison of TENS and massage for pain and range of motion", Physical Therapy, vol. 63, No. 4, published Apr. 1983, pp. 483-493.

B. Sjolund, L. Terenius and M. Eriksson, "Increased cerebrospinal fluid levels of endorphis after electro-acupuncture", Acta Physilogica Scandinavica, vol. 100, published 1977, pp. 382-384.

R. Chen and J. C. Nickel, "Acupuncture Ameliorates Symptoms in Men with Chronic Prostatitis/Chronic Pelvic Pain Syndrome", Urology, vol. 61 (6), published 2003 by Elsevier Inc., pp. 1156-1159.

H. Honjo, K. Kamoi, Y. Naya, O. Ukimura, M. Kujima, H. Kitakoji and T. Miki, "Effects of acupuncture for chronic celvic cain cyndrome with intrapelvic venous congestion: Preliminary results", International Journal of Urology, vol. 11, published 2004, pp. 607-612.

M.I. Johnson, "The clinical effectiveness of TENS in pain management", Critical Reviews in Physical Therapy and Rehabilitation, vol. 12, published 2000, pp. 131-149.

* cited by examiner

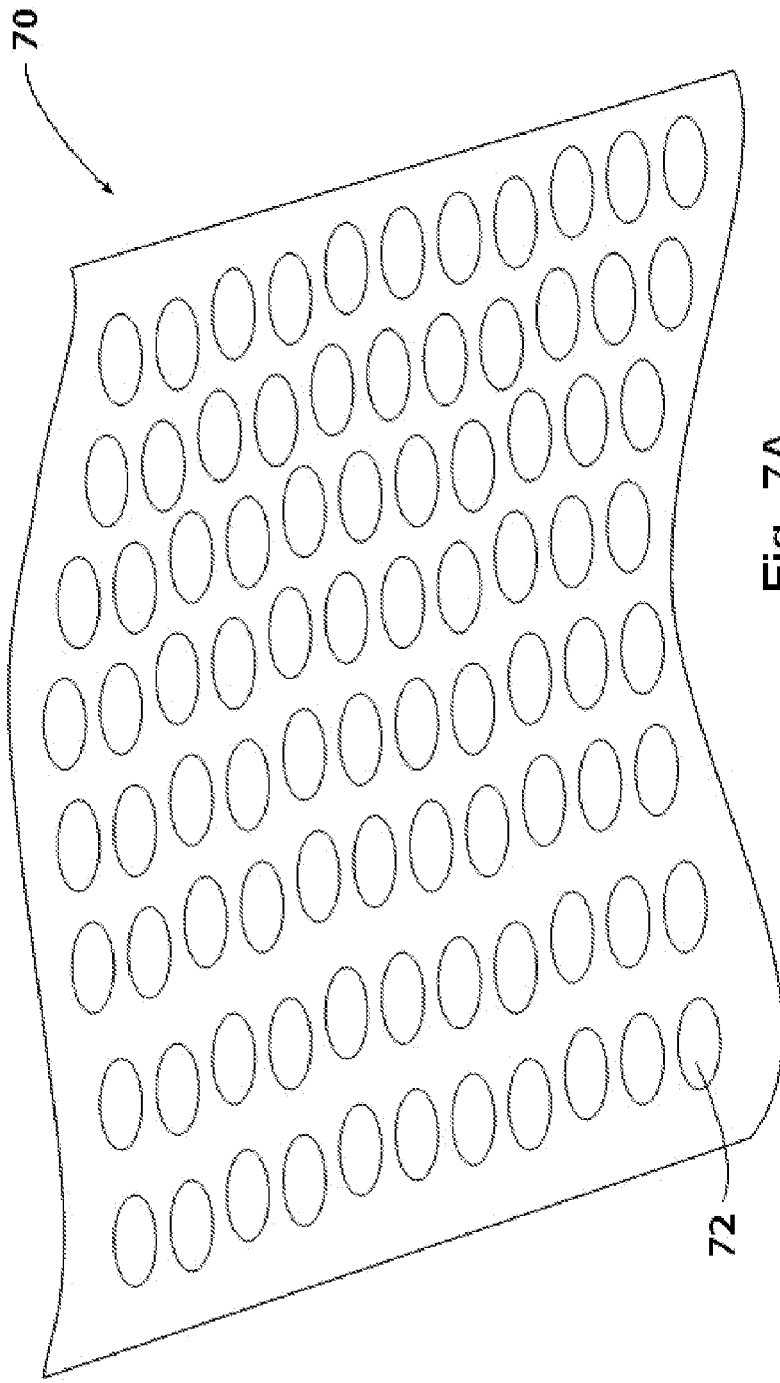
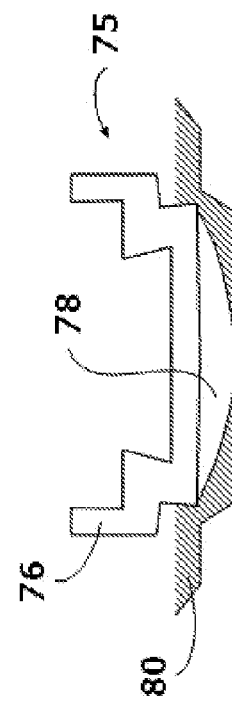
Fig. 7A
Fig. 7B

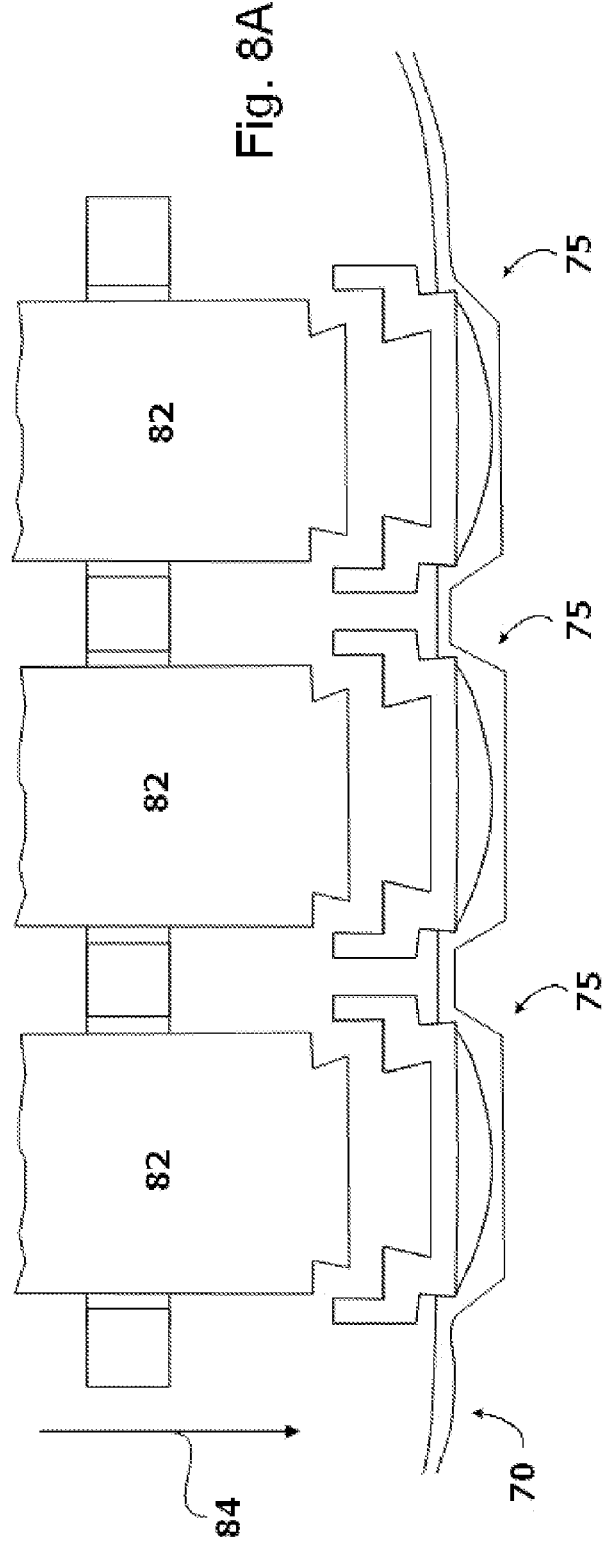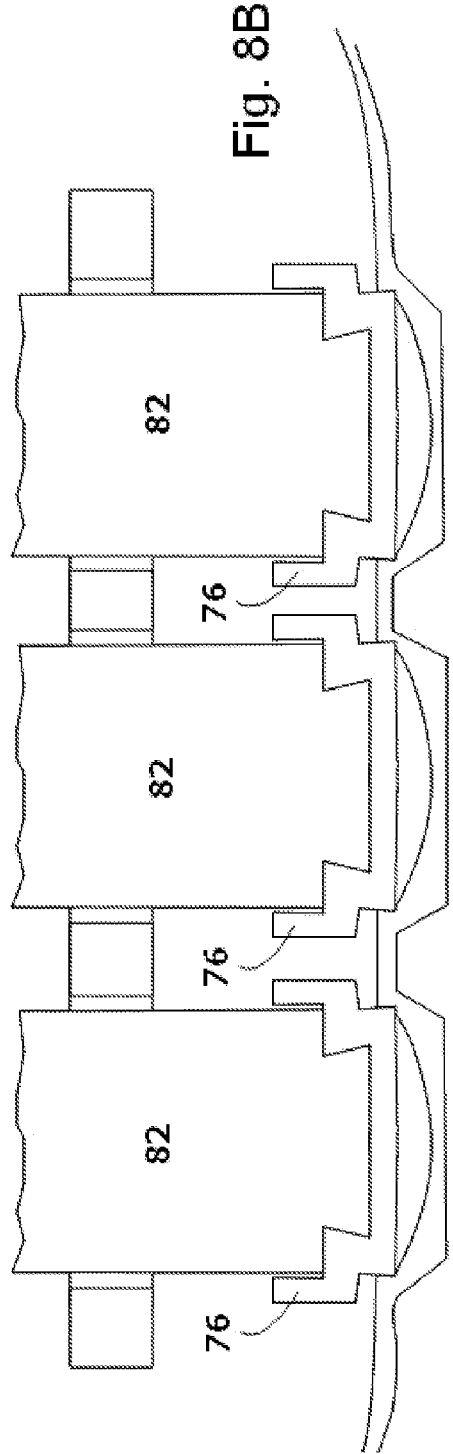

TRANSCUTANEOUS ELECTRICAL THERAPEUTIC DEVICE

CROSS-REFERENCE TO RELATED APPLICATIONS

The present application is a National Phase Application of International Patent Application serial number PCT/IL2007/000661, filed 31 May 2007 and published as WO 2007/138595, entitled "TRANSCUTANEOUS ELECTRICAL THERAPEUTIC DEVICE", which claims the benefit of priority to U.S. Provisional Patent Application Ser. No. 60/809,299, filed 31 May 2006, entitled "Apparatus and method for scanning acupuncture points and applying transcutaneal electrical nerve stimulation"; the aforementioned applications are incorporated herein by reference.

FIELD OF THE INVENTION

The present invention relates to non-invasive/minimally-invasive medical devices and procedures in general. More specifically the present invention relates to an apparatus and method for scanning and localization of therapeutically active points and application of Transcutaneous Electrical Stimulation (TES) to them.

REFERENCES

Cory, P C (1996). Non-invasive, peripheral nerve mapping device and method of use. U.S. Pat. No. 5,560,372.

Cory, P C, Cory, J M (2003). Electrode array and skin attachment system for noninvasive nerve location and imaging device. U.S. Pat. No. 6,564,079.

Floweerdew, M, Gadsby, G (1997). A review of the treatment of chronic low back pain with acupuncture-like Transcutaneous electrical nerve stimulation and Transcutaneous electrical nerve stimulation. *Complementary Therapies in Medicine*. Vol. 5, pp. 193-201.

Gernignani, G, Olivieri, I, Ruju, G, Pasero, G (1991). Transcutaneous electrical nerve stimulation in ankylosing spondylitis: a double-blind study. *Arthritis and Rheumatology*. Vol. 34, pp. 788-789.

Johnson, M I (1998). The analgesic effects and clinical use of acupuncture-like TENS (AL-TENS). *Physical Terapy Reviews*. Vol. 3, pp. 73-93.

Johnson, M I (1997). Transcutaneous electrical nerve stimulation (TENS) in the management of labour pain: the experience of over ten thousand women. *British Journal of Midwifery*. Vol. 5, pp. 400-405.

Johnson, M I (2000). The clinical effectiveness of TENS in pain management. *Critical Reviews in Physical Therapy and Rehabilitation*. Vol. 12, pp. 131-149.

Johnson, M I, Ashton, C H, Thompson, J W (1991). An in-depth study of long-term users of Transcutaneous electrical nerve stimulation (TENS). Implications for clinical use of TENS. *Pain*. Vol. 44, pp. 221-229.

Johnson, M I, Ashton, C H, Thompson, J W (1992). Long term use of transcutaneous electrical nerve stimulation at Newcastle Pain Relief Clinic. *Journal of the Royal Society of Medicine*. Vol. 85, pp. 267-268.

Melzack, R, Vetere, P, Finch, L (1983). Transcutaneous electrical nerve stimulation for low back pain. A comparison of TENS and massage for pain and range of motion. *Physical Therapy*. Vol. 63, pp. 483-493.

Sjölund, B, Terenius, L, Eriksson, M (1977). Increased cerebrospinal fluid levels of endorphis after electro-acupuncture. *Acta Physiologica Scandinavica*. Vol. 100, pp. 382-384.

Chen R, Nickel J C. *Acupuncture Ameliorates Symptoms in Men with Chronic Prostatitis/Chronic Pelvic Pain Syndrome*. Urology. 2003 June; (61)6: 1156-1159.

Honjo H, Kamoi K., Naya Y, et al. *The Effects if Acupuncture for Chronic Pelvic Pain Syndrome with Intravenous Congestion: Preliminary Results*. International Journal of Urology. 2004 August; 11(8): 607-612.

BACKGROUND OF THE INVENTION

Transcutaneous electrical stimulation, (TES), is a non-invasive technique extensively used by numerous health-care providers worldwide. TES includes peripherally applied transcutaneous electrical stimulation as well as transcutaneous electrical stimulation applied to the head, also known as cranial electrical stimulation (CES). According to some prevalent practices TES is applied intended to stimulate the nerves, typically for an analgesic purpose, also known as transcutaneous electrical nerve stimulation or TENS.

TENS uses an electrical current to stimulate peripheral nerves ends and acupuncture points across the surface of the skin. This stimulation achieves proven analgesic effects by activating specific natural pain relief mechanisms. Due to its simplicity, TENS can be administered either in clinics by health-care professionals or at home by patients who have purchased one of the numerous TENS devices available in the market. According to the medical literature, there are over 250,000 TENS units prescribed annually in the United States alone. Its ease of use, general safety and portability make it a preferred treatment, oftentimes more favorable than the long term use of medications and nerve blocks for chronic pain. One of the key aspects of TENS is that the technique is non invasive and has a few side effects when compared with drug therapy.

The proliferation of commercial TENS devices has resulted in numerous variations in terms of the specifics modalities of the treatment. The main types of TENS can be summarized as follows:

conventional TENS—uses high-frequency pulses of relatively low intensity, which stimulate the nerve root, peripheral nerves, or dermatome. Treatment is applied using relatively large electrodes usually placed at appropriate locations on the pain area;

acupuncture-like TENS (ALTENS). ALTENS has two accepted different meanings. According to the first, ALTENS refers to the application of relatively high intensity TENS with high frequency electric pulses. According to the second, ALTENS refers to the delivery of TENS over acupuncture points and not over entire skin regions;

electroacupuncture is quite similar to traditional acupuncture since treatment is applied using needles inserted at specific acupuncture points, along the body. The needles are then attached to a device that generates continuous electric pulses. The frequency and intensity of the current delivered depends on the condition treated;

Intense TENS In this case, the treatment is with high intensity, almost unbearable, electrical current for the treatment.

TES can be also implemented for application of electrical current to trigger points or also myofascial trigger points (henceforth TES of Trigger points or TES-TP). Trigger point therapy, sometimes regarded as one of a group of treatment approaches called neuromuscular therapy, typically involves the application of pressure to tender muscle tissue in order to relieve pain and dysfunction in other parts of the body. It is also referred to as myofascial trigger point therapy.

Known trigger points, acupuncture points, points characterized by proximity to peripheral nerves ends and or other discrete sites on the skin surface of human body that has a presumed capacity to induce whichever therapeutic effect due to TES and or locations characterized by relatively lower local electrical impedance are hereinafter referred to in general as therapeutically active points.

Inter alia, the object of the present invention is to teach a method of locating and or identifying therapeutically active points on the skin surface and applying TES to them.

Particularly, one of the objects of the present invention, is to teach a method of AL-TENS, understood as the delivery of TES over acupuncture points, replacing the traditional needles with localized electrodes or probes. Evidence suggests that AL-TENS produces extra segmental analgesia in a manner similar to that for acupuncture. In two randomized controlled trials in the medical literature the percentage of patients who attain pain relief was found in the range of 88-90% for chronic back pains, better than the placebo effect in this group (40%) and the effect of conventional TENS (50%). The reasons for the better results with this modality in enduring pain relief was explained by the fact that in addition to the nerve stimulation, AL-TENS induces the release of endorphins causing an accumulative effect over time. As compared with traditional acupuncture, AL-TENS is a safer treatment modality eliminating the risks of infection, bruising, organ damage and pneumothorax, needle breakage's, fear of needles, etc.

In order to apply AL-TENS treatment, the acupuncture points on the region of the body of interest must be first located. Numerous point-meters are available in the market for locating these points, using the principle of low impedance at the acupuncture points location. Apparatus for scanning the acupuncture points have been disclosed in the literature. U.S. Pat. No. 6,564,079 discloses an apparatus consisting of an array of electrodes and a skin attachment system for nerve localization. Once a point is located, it is usually marked on the skin surface by using an appropriate marker and then the health-provider decides whether treatment should be applied at such points to achieve the desired analgesic effects. This procedure has several significant drawbacks, information is made necessary relating to finding one point at a time and hence is a time-consuming process; knowledge of acupuncture points location to find the points adequate for the specific pain treatment; marking the points on the skin for later use. This method also entails mechanically marking of the acupuncture points, which is associated with reduced precision and human error. Once an acupuncture point is detected, application of TES requires using an additional apparatus.

A method of scanning for therapeutically active points and application of the therapeutic stimulation of TES by the very same apparatus so far has not been suggested.

Moreover, a method that will provide for scanning of therapeutically active points and subsequent characterization and or identification of the pertinent points, without involvement of a person having knowledge of acupuncture points location, so far has not been suggested either.

SUMMARY OF THE INVENTION

There is provided in accordance with the present invention, an apparatus including patient applied therapeutic module (henceforth PATM), including a fixture and an array of probes housed in the fixture and an actuating controlling module (henceforth ACM). Conjointly, a relative method, characterized by having a data collecting phase and a therapeutic phase, is provided. The method includes the steps of measuring local electrical impedances of a given skin surface area, locating the points characterized by lower impedances, selecting the desired points and applying TES thereto.

BRIEF DESCRIPTION OF THE DRAWINGS

The present invention will be understood and appreciated more fully from the following detailed description taken in conjunction with the appended drawings in which:

FIG. 7A is a schematic representation of exemplary disposable patch;

FIG. 7B is a detailed cross-view diagram of exemplary cap-element;

FIG. 8A is a schematic representation of the probes before they being fastened to the cap-elements;

FIG. 8A is a schematic representation illustrating the action of the fastening mechanism;

Figure 1:
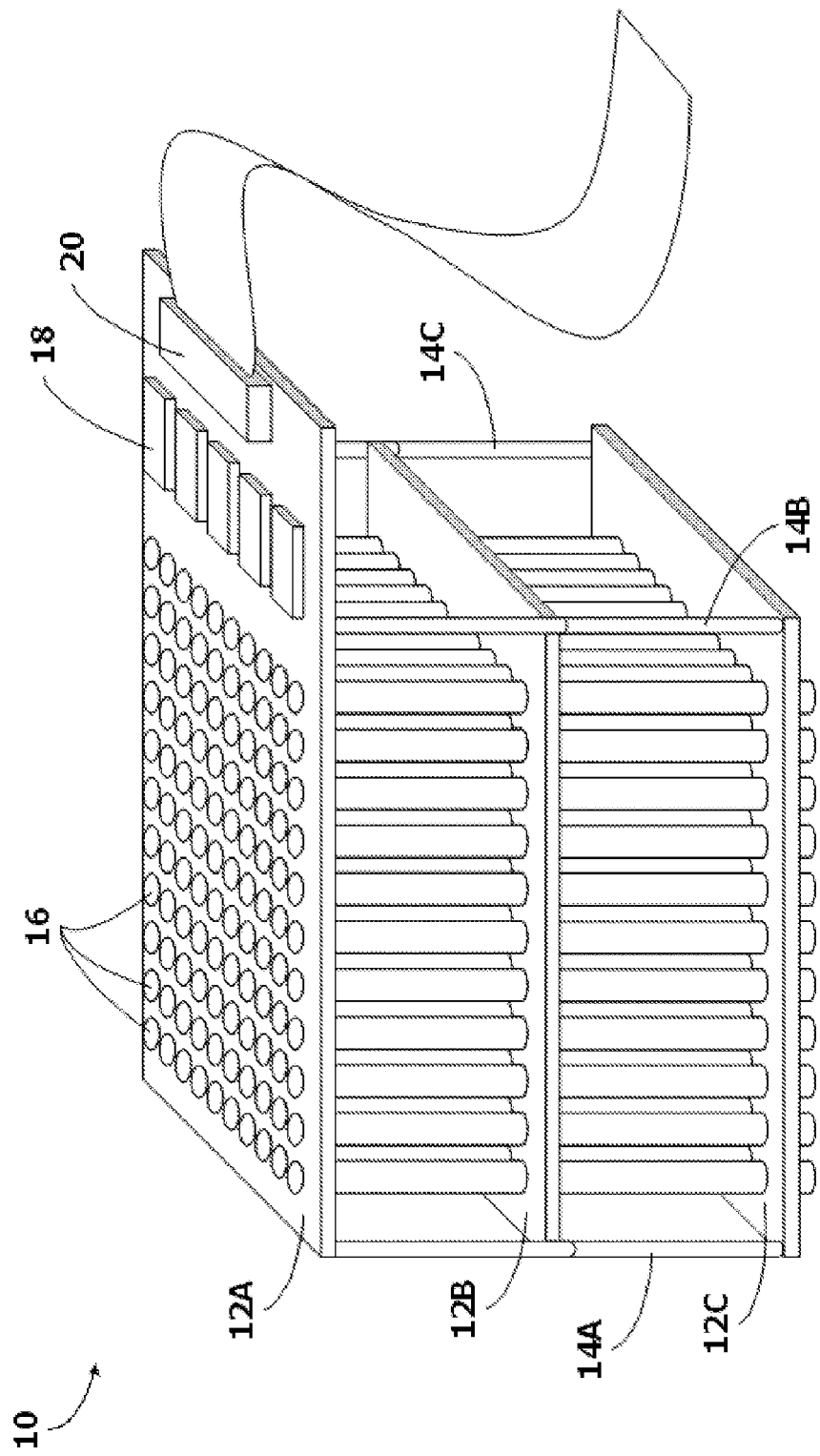
FIG. 1 is an isometric view diagram of an exemplary embodiment of PATM.

While the invention is susceptible to various modifications and alternative forms, specific embodiments thereof have been shown by way of example in the drawings. The components in the drawings are not necessarily to scale, emphasis instead being placed upon clearly illustrating the principles of the present invention. It should be understood, however, that the description herein of specific embodiments is not intended to limit the invention to the particular forms disclosed, but on the contrary, the intention is to cover all modifications, equivalents, and alternatives falling within the spirit and scope of the invention.

DISCLOSURE OF THE INVENTION

Illustrative embodiments of the invention are described below. In the interest of clarity, not all features Illustrative embodiments of the invention are described below. In the interest of clarity, not all features of an actual implementation are described in this specification. It will be appreciated that in the development of any such actual embodiment, numerous implementation-specific decisions must be made to achieve the developers' specific goals, such as compliance with system-related and business-related constraints, which vary from one implementation to another. Moreover, it will be appreciated that such a development effort might be complex and time-consuming, but would nevertheless be a routine undertaking for those of ordinary skill in the art having the benefit of this disclosure.

The apparatus of the present invention includes a patient applied therapeutic module (hereinafter PATM), and an actuating controlling module (henceforth ACM). PATM includes a fixture and a plurality of probes. The probes are contained within the fixture, arranged according to a predetermined pattern, otherwise also known in the colloquial language of the electronics art as "bed of nails".

Reference is now made to FIG. 1, which is a schematic isometric view of an exemplary embodiment of PATM 10. In this example, the fixture consists of parallel plates 12 A-C that are joined together by supportive columns 14 A-C. According to other examples the fixture can be a monolithic unit. Plates 12 A-C can made of any material characterized by substantial firmness, and preferably made of any dielectric material known in the art such as FR4/G10; AT7000™. A two dimensional array of probes 16 is supported by upper plate 12A and guided by the holes in middle and lower plates 12B and 12C respectively, as to be specified below. Upper plate 12A may further support electronic components 18 and connector 20, which connects PATM 10 to the ACM (not shown). In this example, probes 16 are arranged in a predetermined pattern, namely a rectangular pattern of 8 rows and 16 columns; however, any other pattern such as circular, and any number of probes are applicable.

Figure 2:
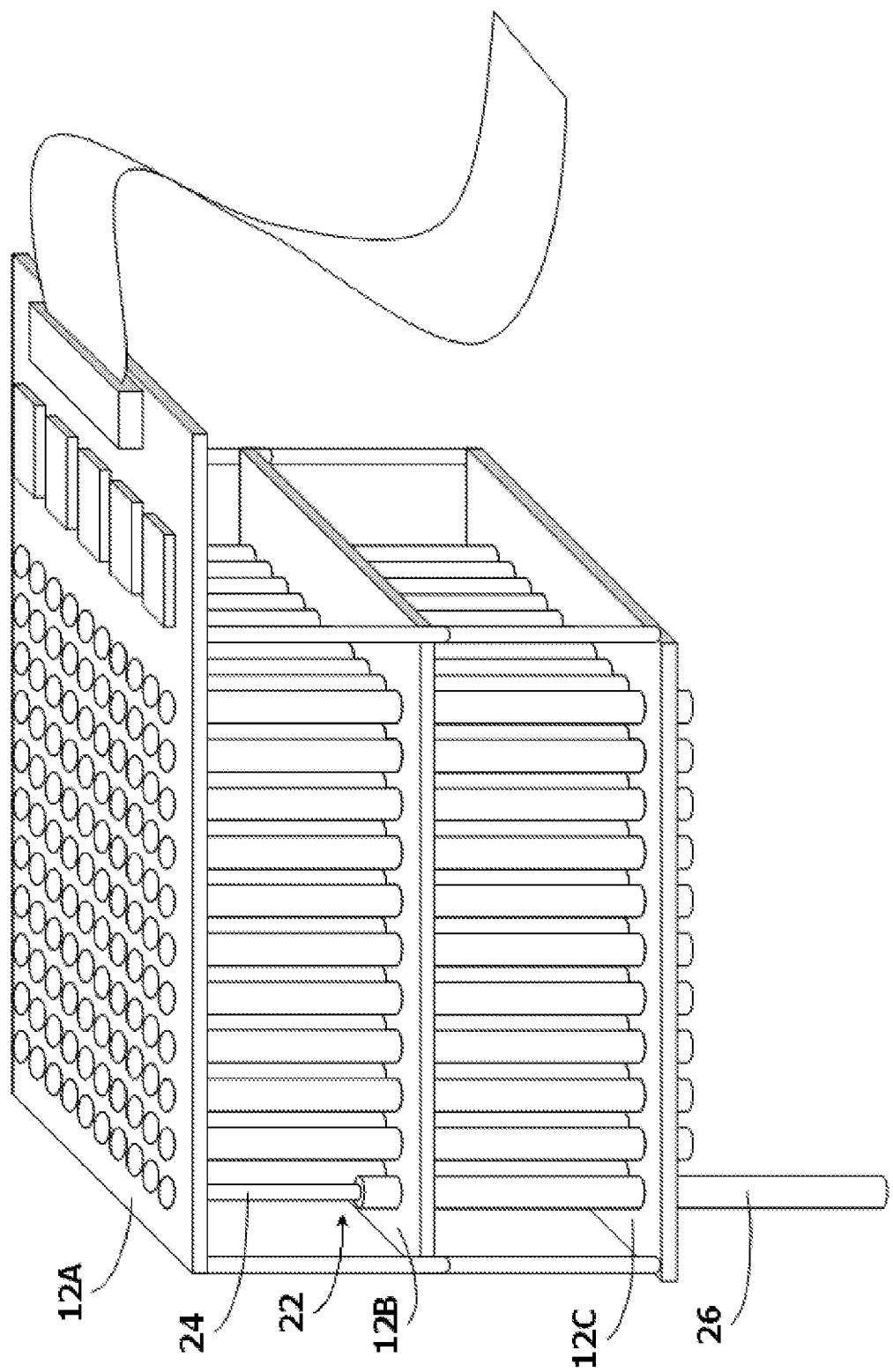
FIG. 2 is an isometric view diagram illustrating extension of a probe.
Figure 3:
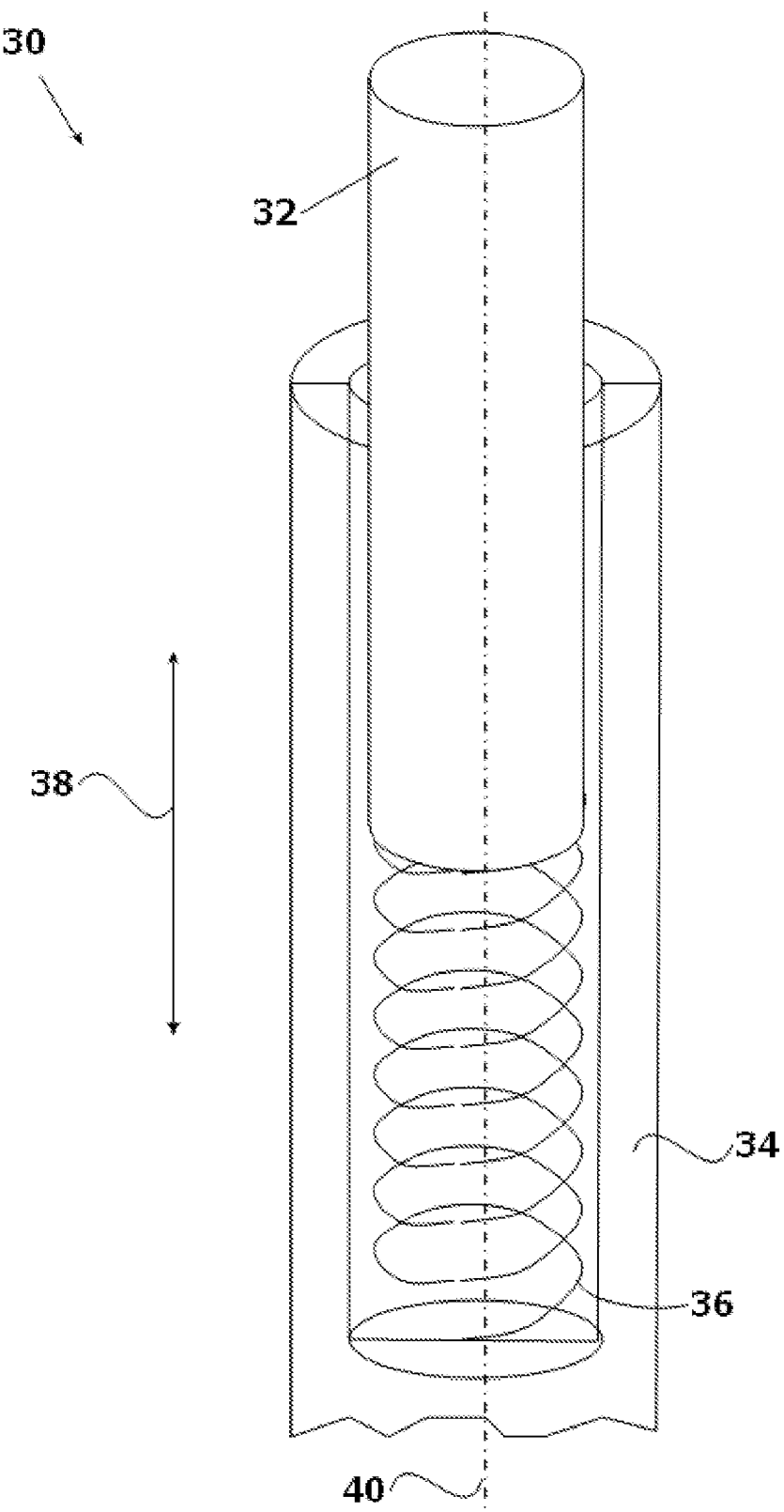
FIG. 3 is schematic cross-view diagram of an exemplary probe.

Reference is now made to FIG. 2, which is an isometric view diagram of an exemplary embodiment of PATM 10 illustrating the extendability of probe 22. In this example probe 22 consists of core 24 and sheath 26. Core 24 can be firmly attached to upper plate 12A and sheath 26 can be urged by an urging means (not shown) to perform translational movement with respect to core 24. Core 24 provides for mechanical support of and substantial electric conductivity with sheath 26, and the translational movement of sheath 26 can be further guided by the holes in middle and lower plates 12B and 12C respectively. The holes in lower plates 12B and 12C may allow sheath 26 to move freely, so that the probes can extend to their full lengths, like probe 22, merely due to the gravitational force. Probes may be further furnished with more elaborate urging means, besides the gravitational force drive their extending. Reference is now made to FIG. 3, which is a schematic cross-view diagram of an exemplary probe 30 consisting of core 32 and sheath 34. Spring 36 urges translational movement of core 32 in direction of arrow 38 along axis 40. A variety of urging means are in accordance with the present invention; examples of urging means include coils or any other resilient constituents, hydraulic and or pneumatic mechanisms, electromagnetic mechanisms, drive by miniature mechanical gears and etc.

Figure 4:
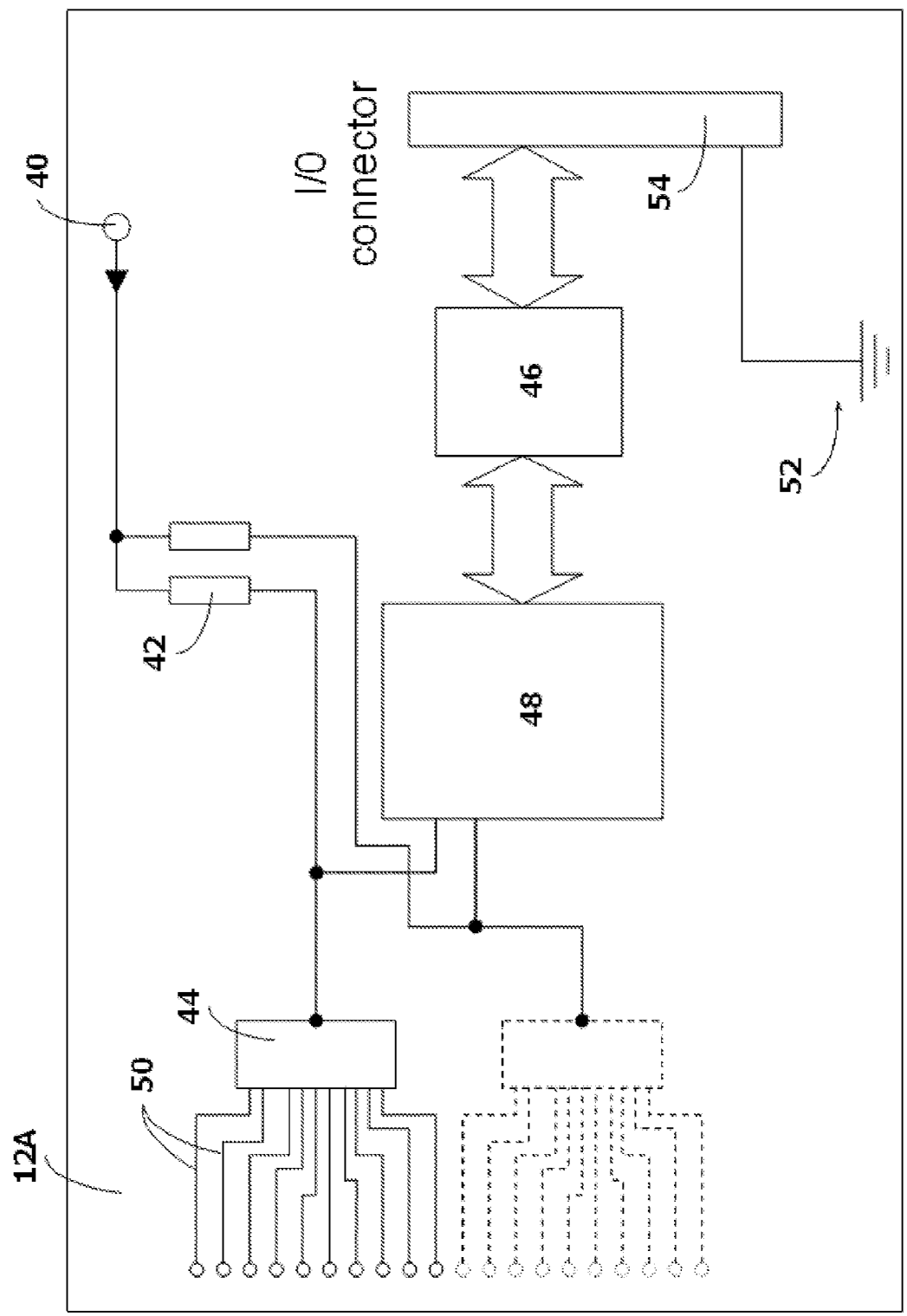
FIG. 4 is schematic diagram illustrating exemplary configuration PATM's electronics.

Reference is now made to FIG. 4 illustrating schematically an exemplary configuration of the electronic circuitry on upper plate 12A. Signal generator 40 is to generate the scanning and treatment electrical signal. The signal is directed to the probes employing resistor 42 and de-multiplexers 44 (hereinafter DEMUX). In this example two branches are shown corresponding each to an array, but any natural number is possible; in some embodiments the number of arrays is 16. In some embodiments, DEMUX is an HCF4097B analogue 8 channel CMOS multiplexer/demultiplexer (ST Microelectronics, Inc.-39, Chemin du Champ des Filles C. P. 21CH 1228 Plan-Les-Ouates GENEVA, Switzerland) with a switching period of at least 50 nano-seconds. The input/output device 46 has a double role, each role associated with a distinct action mode, i.e sensing and switching modes respectively. At the sensing mode, input/output device 46 measures an electric property such as electrical current, associated with the analogue voltage across resistor 42, digitalizes these analogue values and injects the corresponding digital values to the micro-controller 48. At the switching mode, input/output device 46 outputs a digital signal to each one of the DEMUX devices to couple one of channels 50 to signal generator 40. In some embodiments there are 128 channels 50. When a channel is coupled with signal generator 40, electric current for sensing or for treatment can flow through this channel and further through the common ground 52, a return pad (not shown) attached to the body. Micro-controller 48 is connected to ACM (not shown) through input/output connector 54. In some embodiments, micro-controller 48 and input/output device 46 are implemented as one single component. Micro-controller 48 controls the operation of PATM as follows; it commands input/output device 46 to couple a given channel/s 50 with signal generator 40. Micro-controller 48 measures the voltage drop at resistor 42.

Figure 5:
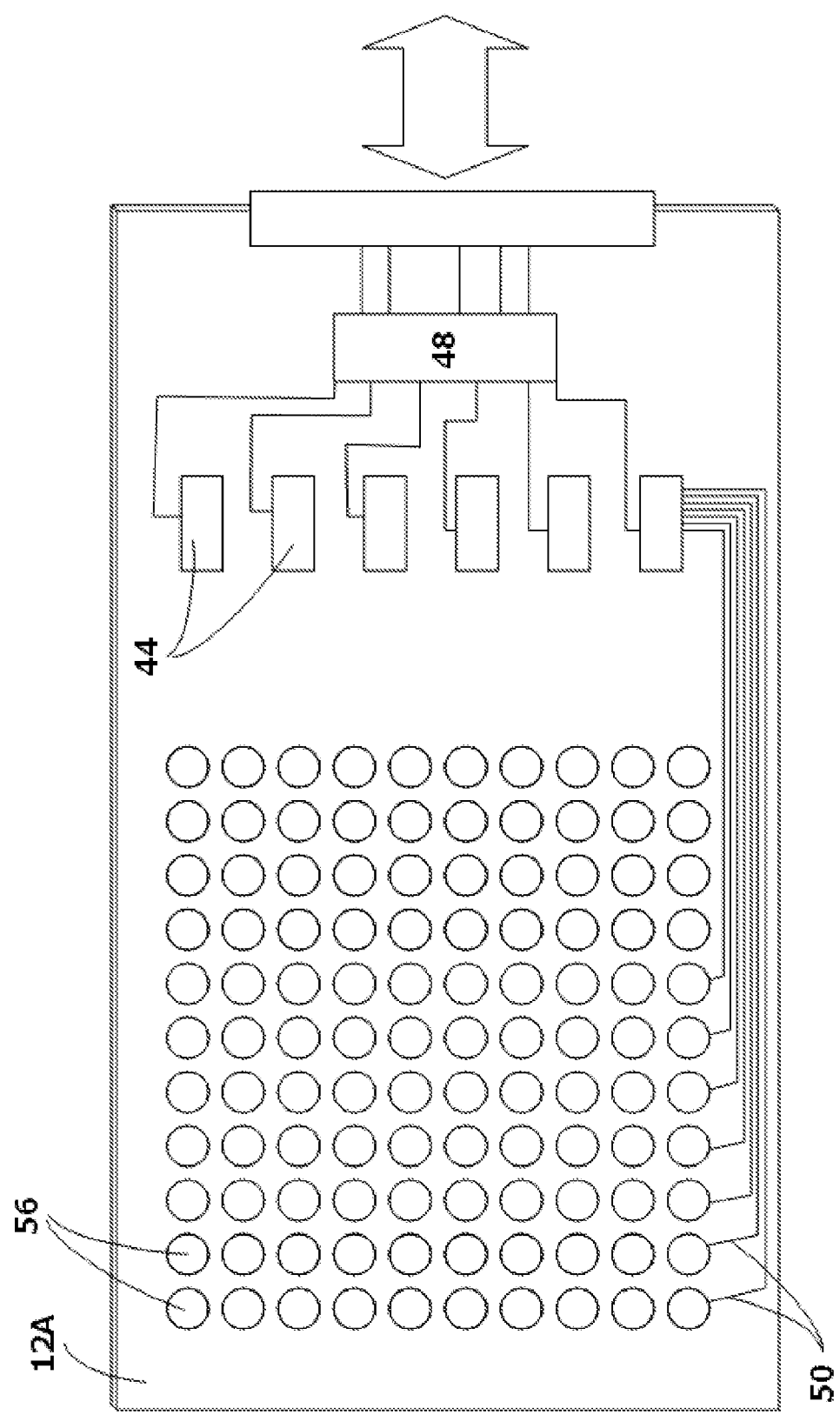
FIG. 5 is schematic diagram of exemplary outline of PATM's circuit topography.

Reference is now made to FIG. 5 schematically illustrating exemplary components and circuitry of upper plate 12A. Micro-controller 48 is electrically connected to DEMUXs 44. Each one of output channels 50 of each DEMUX 44 is connected by means of wire to a plurality of connectors 56. Each connector 56 is electrically connected to a corresponding probe of an array of probes 16 as shown in FIG. 1 to which reference is again made. Referring again to FIG. 5, connectors 56 provide for mechanical support of the probes and a low impedance connection between the output channels and the probes.

Figure 6:
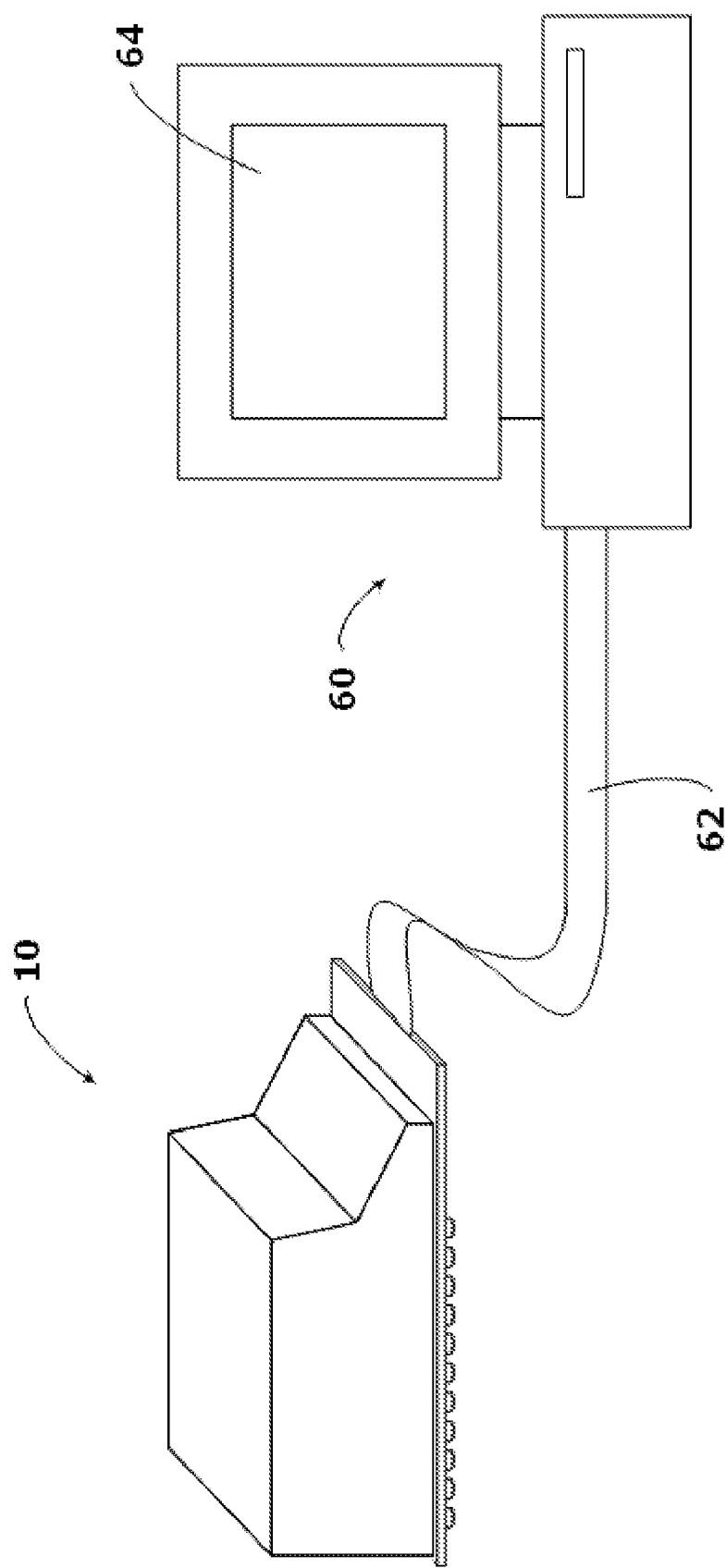
FIG. 6 is schematic diagram illustrating the set-up of the system of the present invention.

Reference is now made to FIG. 6 schematically illustrating a functional set-up embodying the present invention. In the set-up PATM 10 is connected to ACM 60 by means of cable 62. ACM 60, typically a personal computer, includes a graphical user interface (GUI) 64 and a memory storage medium (not shown).

According to the present invention, the distal end of the probes, such as the distal end of sheath 26 of probes 22 protruding from the lower plate as described above with reference to FIG. 2, to which reference is made again are to be brought into physical contact with the patient's skin at a point of contact (hereinafter referred to as contact site or CS) so as to facilitate effective and uniform electrical conductivity between the each single probe and patient's body. A possible problem underlying the facilitation of an effective electrical conductivity at CS is a potentially high and non-uniform electrical resistance of the skin. This non uniformity is associated among other factors, with the coarseness and or moistness pattern of the skin, structural and or morphological aspects.

Several approaches to overcome the aforementioned potential conductivity inconsistency are disclosed below. According to some embodiments, the distal end of the probes is shaped having pointed or sharp tip or edge facing the skin, characterized by relatively small surface area, which results in relatively high pressure applied on the skin at the CS, resulting in a better and more uniform electrical conductivity.

According to some other embodiments, the distal end of the probes is further furnished with a miniature needle that penetrates the epidermis and or dermis and thus precludes the problems associated with surficial variability.

According to yet other embodiments, the distal end of the probe is further furnished with cap-elements and or covered with a layer of material characterized by substantial elasticity and electrical conductivity. The elastic properties of the cap-element or and of the layer covering the distal ends of the probes provide for physical contact with the skin surface and thus facilitate more uniform and significantly lower electrical resistance at the CS. Examples of such electrically conductive and elastic materials include, inter alia, hydrogels. A particular example of a hydrogel material is a composite of polyaniline nanoparticles and poly(N-vinyl-2-pyrrolidone). It should be stressed, however, that any materials characterized by substantial elasticity and electrical conductivity applicable.

According to some embodiments, the electrically conductive elastic material (hereinafter ECEM) is applied, optionally in a reversible manner, onto the distal ends of the probes, as a covering stratum by brushing, smearing or spraying. Alternatively, the ECEM can be applied by immersing the distal ends of the probes into the ECEM. In such a case, complimentary baths and forms for exposing exclusively the tips of the probes are disclosed.

According to some preferred embodiments, an ECEM is provided in the form of cap-elements fastened, preferably in a reversible manner, to the tips of the probes. In some examples, an array of such cap-elements is arranged in a form of a disposable patch, applied to PATM prior to the treatment session. Reference is now made to FIG. 7A, which is a schematic representation of exemplary disposable patch 70, wherein a plurality of cap-elements 72 are embedded, corresponding the pattern in which the probes of PATM (not shown) are arranged. Reference is now made to FIG. 7B, which shows a cross-sectional view of exemplary cap-element 75, wherein fastening portion 76 and CS portion 78 form a continuum with each other. Protective layer 80 can be optionally employed for covering CS portion 78 and embracing fastening portion 76.

Figure 9:
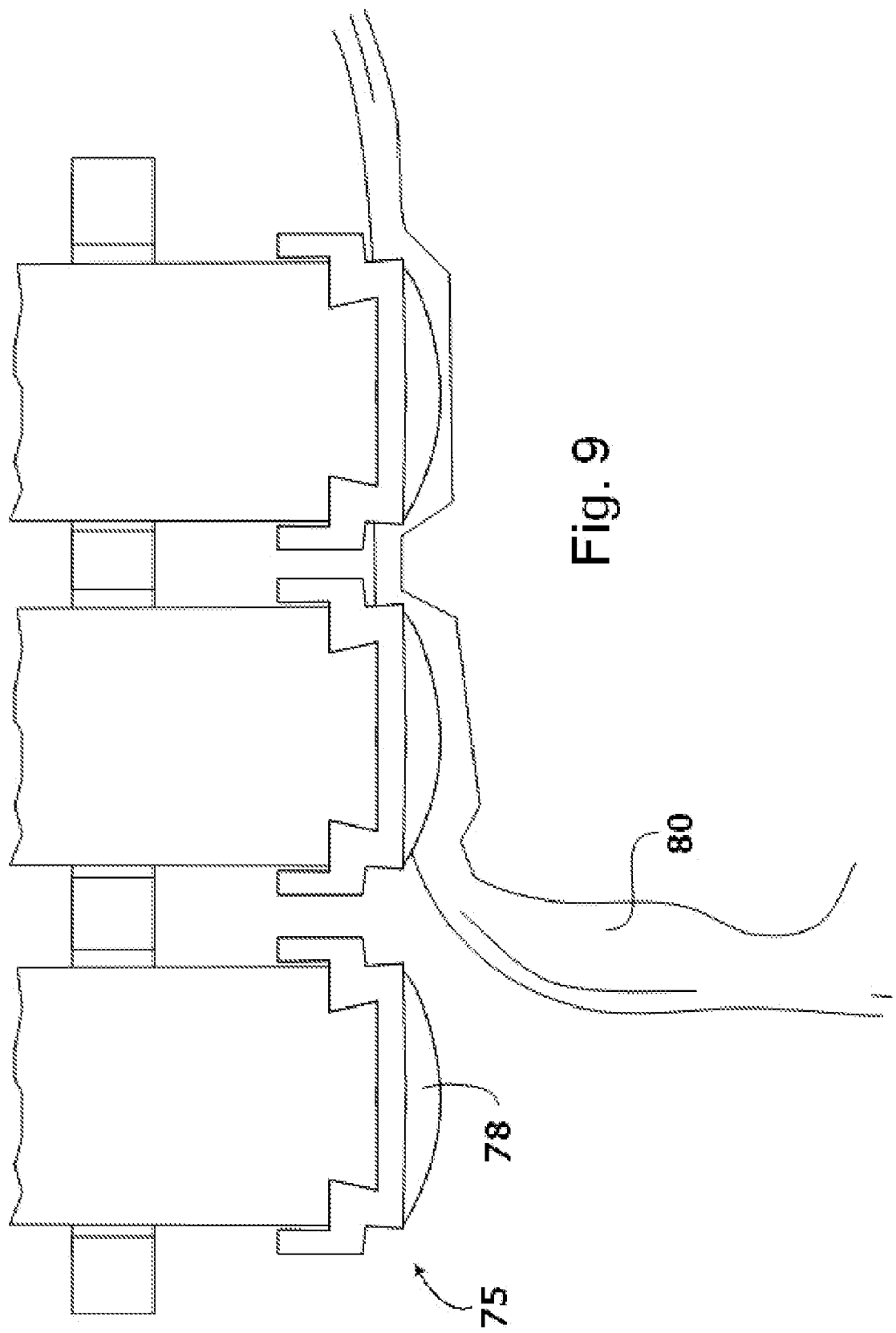
FIG. 9 is a schematic diagram illustrating removal of the protective layer from the cap-elements.

Reference is now made to FIGS. 8A and 8B, which is a schematic representation of an exemplary fastening mechanism, providing for removably attaching probes 82 to cap-elements 75. Initially, probes 82 are aligned with disposable patch 70 in such a manner that the tips of the probes correspond the locations of cap-elements 75. Probes 82 are then urged in direction of arrow 84 towards disposable patch 70, or vise versa; after which fastening portions 76 are subsequently fastened to the tips of probes 82. Subsequently, as can be seen in FIG. 9 to which reference is now made, Protective layer 80 is then removed, exposing CS portions 78 of cap-elements 75.

Figure 10:
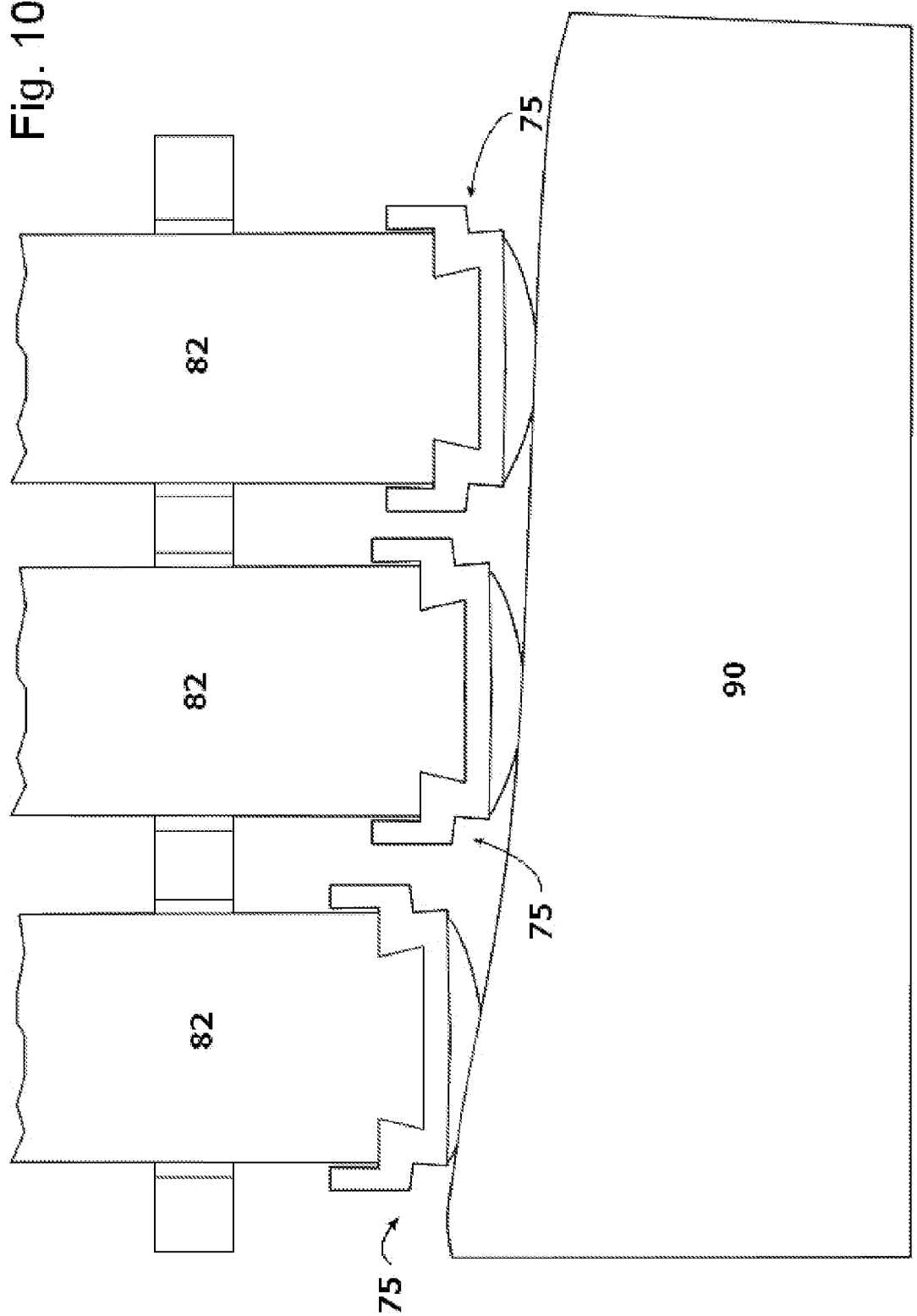
FIG. 10 illustrating application of cap-elements onto structured relief of patient's skin.

Reference is now made to FIG. 10, illustrating application of cap-elements 75, onto a relief of patient's skin 90. Cap-elements 75 on probes 82 are pressed against patient's skin 90 and adjustably adjoin the relief of skin 90, facilitating lower and more uniform electrical resistance at the CS.

Figure 11:
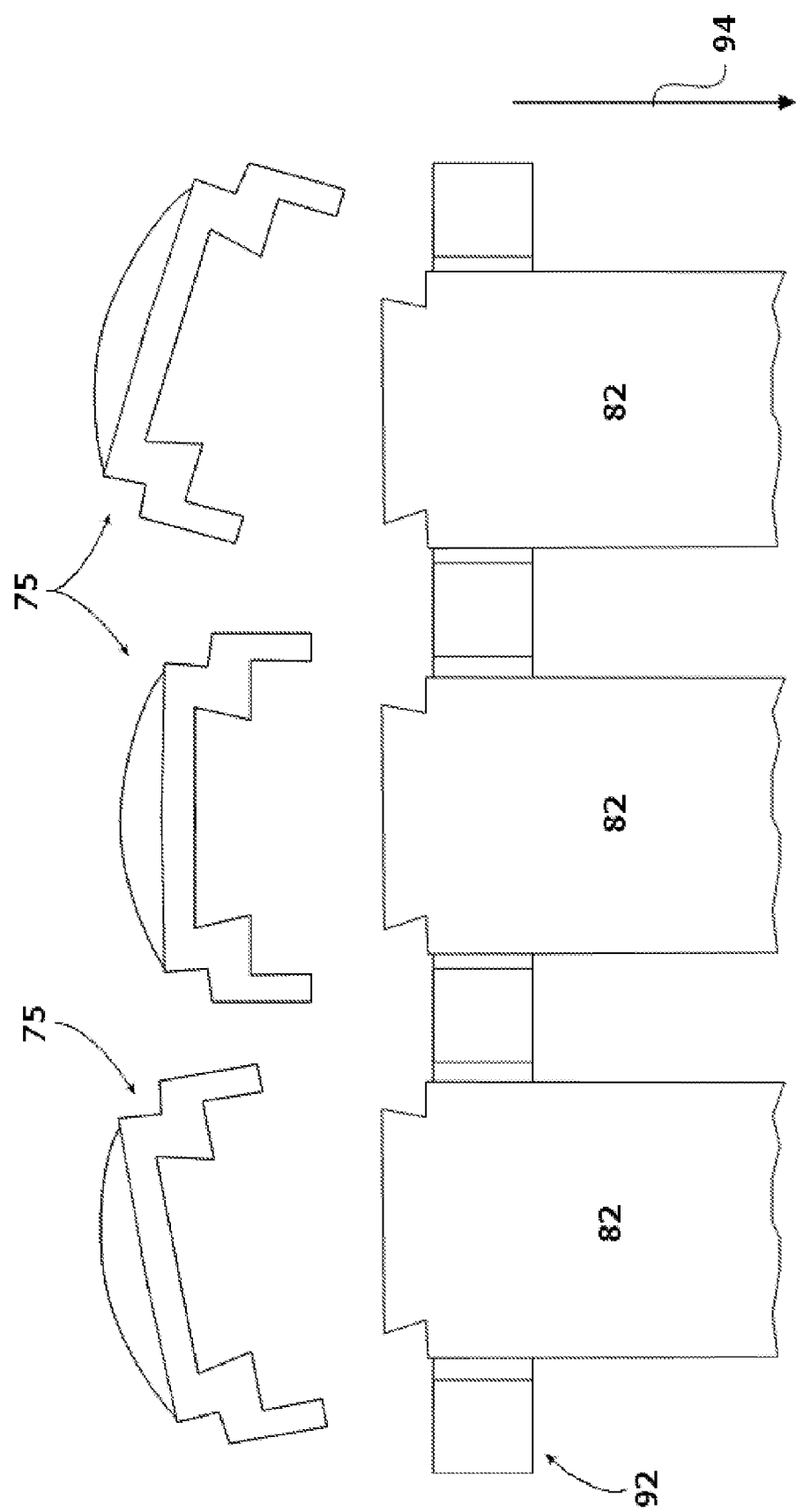
FIG. 11 illustrating the detachment of cap-elements from the probes.

Reference is now made to FIG. 11, illustrating the detachment of cap-elements 75 from probes 82. Probes 82 are retracted into PATM 92 in direction of arrow 94 and cap-elements 75, having bigger exterior circumference than the holes of probes 82, are pushed off by the surface of PATM 92.

According to the method of the present invention, PATM is placed on the area of interest on the skin surface of patient's body and further optionally attached to the body so as to substantially immobilize the PATM relative to the body. In a preferred embodiment of the present invention, an area of interest is the center of the lower back of the patient's body, with the lower end located at the upper sacrum; exemplary PATM that can be employed for treating this area is 20 cm wide and 40 cm long, with 2048 pins arranged in 32 columns with 64 pins each column. The probes of PATM are then brought into contact with patient's skin, and optionally a return pad, for common ground attached to the body.

Using the input/output device, scanning is initiated. Throughout the scanning, the micro-controller is activated in the sensing mode to couple each one of the probes to the signal generator one at a time, while concurrently measuring the drop voltage across the corresponding resistor. The effective voltage drop for each probe is stored in the memory storage medium of the ACM; and locations of point of high voltage drops, corresponding to high current flow, and hence to low impedance at a given point, are interpreted as associated with potentially active therapeutic points.

According to some embodiments of the method of the present invention, at the memory storage medium of ACM are conjointly stored predetermined locations of known therapeutically active points on the skin surface of the human body, including acupuncture points, preferably arranged in maps, and optionally classified according to the effect which application of treatment on these points is to produce. Optionally, complimentary measurements of the patient's body are made so that the map can be adjusted to the scale of the patient under treatment. In some preferred embodiments, the sex, height, and circumference of the body, for instance at the fifth lumbar vertebrae, are measured and fed into the ACM. The relative locations of potentially active therapeutic points, found during the scanning, are then superimposed with the predetermined locations of known therapeutically active points, at the region where PATM was applied, stored at the memory storage medium of ACM.

The therapeutically active points available for application of the TES are then identified and presented to a human operator on GUI. Desired therapeutically active point/s are then selected by the human operator, and parameters of TENS to be applied such as duration, intensity, repetitiveness, etc. are determined. According to some preferred embodiments, GUI is a touch-screen device optionally furnished with a touch pen. After selecting the points and determining aforementioned parameters, a switching mode is invoked by using the input/output device, during which the channel corresponding the probe at the therapeutically active point, whereto treatment to be applied, is coupled with the signal generator.

APPLICATIONS OF THE INVENTION

Application of the TES to whichever of the following: all known trigger points, acupuncture points, points characterized by proximity to peripheral nerves ends and or other discrete sites on the skin surface of human body that has a presumed capacity to induce whichever therapeutic effect due to TES and or locations characterized by relatively lower local electrical impedance, is in accordance with the present invention and constitute an adequate application thereof.

The system of the invention is applicable in therapeutic indications as follows. Pain treatment: back pain, carpal tunnel syndrome, headache, scar pain, Fibromyalgia, neck pain, face pain, shoulder pain, elbow pain, wrist pain, hip pain, knee pain, ankle pain, arthritic pain, peripheral neuropathy, prostatitis and pelvic pain. Indications associated with cancer treatment: anesthesia, post-operative pain control, nausea and vomiting, hastening recovery from the side effects of the various therapies.

It will be appreciated that the present invention is not limited by what has been particularly described and shown hereinabove and that numerous modifications, all of which fall within the scope of the present invention, exist. Rather the scope of the invention is defined by the claims which follow:

The invention claimed is:

1. An apparatus for locating therapeutically active points and applying transcutaneous electrical stimulation thereto, said apparatus comprising:
   a patient applied therapeutic module (PATM), said PATM comprising:
   i. a plurality of probes, each of said probes extendable along a longitudinal axis thereof,
   ii. a fixture arranged to secure said probes in at least one array, and further arranged to allow each of said probes to extend longitudinally up to a respective maximum length as a translational movement with respect to said fixture, said longitudinal extension of each of said probes being independent of the longitudinal extension translational movement and length of any other of said probes, and an electronic circuitry comprising a signal generator and arranged to sense the impedance associated with each of said probes; and an actuating controlling module (ACM) in communication with said electronic circuitry of said PATM, said ACM comprising:
  i. a graphical user interface, and
  ii. a memory storage medium;

wherein, said ACM is arranged to receive from said PATM said sensed impedance associated with each of said probes, store said received impedances on said memory storage medium and display, utilizing said graphical user interface, relative locations of active therapeutic points responsive to said stored received impedances.

2. The apparatus for locating therapeutically active points and applying transcutaneous electrical stimulation thereto as in claim 1, wherein said PATM is further arranged to provide transcutaneous electrical stimulation from said signal generator to each of said probes, independently from all other of said probes, responsive to said ACM.

3. The apparatus for locating therapeutically active points and applying transcutaneous electrical stimulation thereto as in claim 1, wherein said PATM further comprises a means for attaching said therapeutic module to a patient body.

4. The apparatus for locating therapeutically active points and applying transcutaneous electrical stimulation thereto as in claim 1, wherein the length of longitudinal extension of each of said probes is to a length sufficient such that a distal end of each of said probes physically adjoins a skin surface of a patient body and is in electrical contact with the patient skin surface to which it is physically adjoined.

5. The apparatus for locating therapeutically active points and applying transcutaneous electrical stimulation thereto as in claim 4 further comprising an electrically conductive return pad arranged for physical attachment to the patient body.

6. The apparatus for locating therapeutically active points and applying transcutaneous electrical stimulation thereto as in claim 1, further comprising a resistor arranged in series with the signal generator during said sensing of the impedance, said PATM further comprising an input/output device arranged to measure an electrical property associated with the voltage drop across the resistor, the sensed impedance a function of the measured electrical property.

7. The apparatus for locating therapeutically active points and applying transcutaneous electrical stimulation thereto as in claim 4, wherein said distal ends of said probes have a structural characteristic selected from the group consisting of: a pointed tip, a sharp edge and a miniature needle.

8. The apparatus for locating therapeutically active points and applying transcutaneous electrical stimulation thereto as in claim 4, wherein said probes, at said distal ends, are further covered by a stratum of electrically conductive elastic material.

9. The apparatus for locating therapeutically active points and applying transcutaneous electrical stimulation thereto as in claim 8, wherein said stratum of electrically conductive elastic material comprises a hydrogel.

10. The apparatus for locating therapeutically active points and applying transcutaneous electrical stimulation thereto as in claim 4, wherein said probes, at said distal ends, are further furnished with cap-elements characterized by substantial electrical conductivity and elasticity.

11. The apparatus for locating therapeutically active points and applying transcutaneous electrical stimulation thereto as in claim 10, wherein said cap-elements each have a fastening portion and a contact site portion.

12. The apparatus for locating therapeutically active points and applying transcutaneous electrical stimulation thereto as in claim 10, wherein an array of said cap-elements are embedded in a detachable patch of protective layer in a predetermined arrangement pattern.

13. The apparatus for locating therapeutically active points and applying transcutaneous electrical stimulation thereto as in claim 2, further comprising a resistor arranged in series with the signal generator, said PATM further comprising an input/output device arranged to measure an electrical property associated with the voltage drop across said resistor during said impedance sensing and during said provided transcutaneous electrical stimulation.

14. The apparatus for locating therapeutically active points and applying transcutaneous electrical stimulation thereto as in claim 4, further comprising a resistor arranged in series with the signal generator, said PATM further comprising an input/output device arranged to measure an electrical property associated with the voltage drop across said resistor during said impedance sensing and during said provided transcutaneous electrical stimulation.

15. The apparatus for locating therapeutically active points and applying transcutaneous electrical stimulation thereto as in claim 1, wherein each of said probes are urged to extend longitudinally merely due to gravitational force.

* * * * *